United States Patent [19]

Suzuki et al.

[11] Patent Number: 4,822,933

[45] Date of Patent: Apr. 18, 1989

[54] PROCESS FOR PRODUCING A CHLOROHALOBENZENE

[75] Inventors: Toshihiro Suzuki; Yasushi Higuchi, both of Shizuoka, Japan

[73] Assignee: Ihara Chemical Industry Co., Ltd., Tokyo, Japan

[21] Appl. No.: 120,171

[22] Filed: Nov. 12, 1987

Related U.S. Application Data

[63] Continuation of Ser. No. 857,519, Apr. 23, 1986, abandoned, which is a continuation of Ser. No. 585,254, Mar. 1, 1984, abandoned.

[30] Foreign Application Priority Data

Mar. 7, 1983 [JP] Japan .................. 58-36847

[51] Int. Cl.$^4$ .................. C07C 17/12; C07C 17/24
[52] U.S. Cl. .................. 570/208; 570/206; 570/207
[58] Field of Search .................. 570/207, 208, 206

[56] References Cited

U.S. PATENT DOCUMENTS

| | | | |
|---|---|---|---|
| 2,998,459 | 8/1961 | Baker et al. | 570/207 |
| 3,140,253 | 7/1964 | Plank et al. | 502/73 |
| 3,471,412 | 10/1969 | Miale et al. | 502/73 |

FOREIGN PATENT DOCUMENTS

| | | | |
|---|---|---|---|
| 0118851 | 9/1984 | European Pat. Off. | 570/208 |
| 195514 | 9/1985 | European Pat. Off. | 570/208 |
| 0171265 | 2/1986 | European Pat. Off. | 570/208 |
| 0225723 | 6/1987 | European Pat. Off. | 570/208 |
| 2087536 | 4/1987 | Japan | 570/208 |
| 650985 | 3/1979 | U.S.S.R. | 570/208 |

OTHER PUBLICATIONS

*Journal of Catalysis* (1979), 60, 110–120.
*Tetrahedron Letters* (1980), 21, pp. 3809–3812, Huizinga et al.
*Recueil* (1974), 93, 72.

*Primary Examiner*—Werren B. Lone
*Attorney, Agent, or Firm*—Oblon, Fisher, Spivak, McClelland & Maier

[57] ABSTRACT

A process for producing a chlorohalobenzene represented by the general formula:

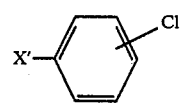

(I)

where X′ is a halogen atom, by chlorinating a benzene represented by the general formula:

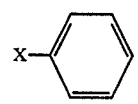

(II)

where X is a hydrogen atom or a halogen atom, in a liquid phase in the presence of a catalyst, characterized in that L-type zeolite is used as the catalyst.

15 Claims, No Drawings

PROCESS FOR PRODUCING A CHLOROHALOBENZENE

This application is a continuation of application Ser. No. 857,519, filed on Apr. 23, 1986, now abandoned, which is a continuation of application Ser. No. 585,254, filed Mar. 1, 1984, now abandoned.

BACKGROUND OF THE INVENTION

1. Field of the Invention

The present invention relates to a process for producing a chlorohalobenzene. More particularly, it relates to a process for producing a p-chlorohalobenzene with high selectivity by chlorinating a benzene with use of a specific catalyst.

Chlorohalobenzenes are useful as solvents or starting materials for medicines, agricultural chemicals and various other organic synthetic compounds. Particularly, there are strong demands for p-dichlorobenzene.

2. Description of the Prior Art

As a process for the production of chlorohalobenzenes, it has been known to produce dichlorobenzenes by chlorinating benzene or chlorobenzene with use of a Lewis acid such as antimony pentachloride, ferric chloride or aluminum chloride as the catalyst. However, such a process produces not only p-dichlorobenzene but also its isomers such as o- and m-dichlorobenzenes and polychloro- substituted products such as trichlorobenzene, whereby it is impossible to produce p-dichlorobenzene with high selectivity in good yield as high as at least 60%.

Then various catalysts have been proposed to produce p-dichlorobenzene in better yield. For instance, in a process for chlorinating chlorobenzene with chlorine in the presence of an iron sulfide catalyst, p-dichlorobenzene is obtainable in a yield of from 60 to 70% (Japanese Unexamined Patent Publication No. 64231/1975), and in a process for the chlorination with chlorine with use of selenium or a selenium compound as the catalyst, p-dichlorobenzene is obtainable in the maximum yield of 72% (Japanese Examined Patent Publication No. 34010/1975). However, these processes do not provide adequate selectivity for the production of p-dichlorobenzene.

Further, it has been proposed to use X-type zeolite as a catalyst for a vapor phase chlorination for the production of p-dichlorobenzene (Japanese Unexamined Patent Publication No. 77631/1982). However, in such a vapor phase chlorination, the conversion is as low as 48.3% at best. An attempt to improve the conversion is likely to facilitate a side reaction as well, whereby the production of an undesirable trichloro-derivative will be increased.

Under these circumstances, the present inventors have conducted extensive researches and have unexpectedly found that by using L-type zeolite as a catalyst for the liquid phase chlorination of a benzene, it is possible not only to solve the difficulties inherent to the conventional processes but also to produce p-dichlorobenzene with substantially higher selectivity than the conventional processes. The present invention has been accomplished based on this discovery.

Namely, the present invention provides a process for producing a chlorohalobenzene represented by the general formula:

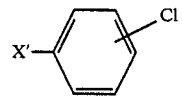     (I)

where X' is a halogen atom, by chlorinating a benzene represented by the general formula:

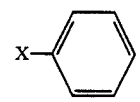     (II)

where X is a hydrogen atom or a halogen atom, in a liquid phase in the presence of a catalyst, characterized in that L-type zeolite is used as the catalyst.

Now, the present invention will be described in detail with reference to the preferred embodiments.

As the benzene of the general formula II to be used as the starting material in the process of the present invention, there may be mentioned benzene, chlorobenzene, bromobenzene, fluorobenzene or iodobenzene.

The L-type zeolite to be used in the process of the present invention, is preferably a crystalline alumina silicate having a molar ratio of silicon oxide. $(SiO_2)$/aluminum oxide $(Al_2O_3)$ being from 4 to 8. In general, there may be used synthetic or natural zeolite having the same X-ray diffraction spectrum as such crystalline alu-ina silicate. It is common to use L-type zeolite in which the ion exchangeable cation is potassium. In this case, potassium may be ion exchanged by sodium. A conventional ion-exchange method may optionally by employed for such ion exchange. Usually, the ion exchange can readily be done by treating the potassium-containing L-type zeolite with an aqueous solution of sodium nitrate or chloride. The L-type zeolite of the present invention may of course contain, in addition to potassium ions, other cations. For instance, it is preferred to employ L-type zeolite substituted with a metal belonging to Group IA, IIA, IIIA, IVA or VA, a transition metal or a proton. These cations may be incorporated alone or in combination as a mixture of two or more. The catalyst may be calcined or uncalcined.

To conduct the chlorination of a benzene in accordance with the process of the present invention, the L-type zeolite is addedd in an amount of at least 0.1 g, preferably from 0.1 to 50 g, more preferably from 1 to 30 g, per mol of the benzene so that the mixture can be stirred, and a chlorinating agent is introduced at a temperature of not higher than the boiling point of the benzene. If desired, a solvent may be used for the reaction. For the industrial operation, the reaction is usually conducted at a temperature within a range of from 0° C. to the boiling point of the benzene, preferably from 20 to 90° C. For this reaction, it is possible to use a chlorinating agent which is commonly employed for the chlorination. For instance, there may be mentioned chlorine gas, sulfuryl chloride, N-chlorosuccimide, phosphorus pentachloride or chlorine monoxide. Particularly preferred is chlorine gas. Further, an inert gas such as nitrogen may be used for the reaction. The reaction may be conducted under reduced or elevated pressure, but is usually conducted under atmospheric pressure.

According to the process of the present invention, it is possible to selectively and efficiently chlorinate the p-position of the benzene while suppressing the chlorination at the o-position and to minimize the formation of tri- or higher halides. Further, the operation of the reaction and the after-treatment is simple, and the catalyst can be reused. Thus, the process is suitable for the production of p-chlorohalobenzenes and extremely effective particularly when used for the production of p-dichlorobenzene.

Now, the present invention will be described in further detail with reference to Examples. However, it should be understood that the present invention is by no means restricted by these specific Examples.

EXAMPLE 1

Into a 200 ml reaction flask equipped with a condenser, a thermometer, a stirrer and a gas supply tube, 5 g of L-type zeolite (tradename: TSZ-502, manufactured by Toyo Soda Manufacturing Co., Ltd.) and 78.1 g (1 mol) of benzene were introduced and stirred for 30 minutes at 70° C. under a nitrogen gas stream. Then, chlorine was supplied at a rate of 0.25 mol/hr for 8 hours to conduct the reaction. After the completion of the reaction, the reaction solution thereby obtained, was analysed by gas chromatography, whereby it was found that the conversion of benzene was 100%, the yield of p-dichlorobenzene was 87.8%, the production ratio of o-dichlorobenzene/p-dichlorobenzene (i.e. o/p ratio) was 0.124, and trichlorobenzene was 0.6%.

The L-type zeolite used for the reaction, had the following chemical composition (as measured by an atomic absorptiometric method).

| | | |
|---|---|---|
| $SiO_2$ | 64.6% by weight | (dry base) |
| $Al_2O_3$ | 17.8% by weight | (dry base) |
| $Na_2O$ | 0.15% by weight | (dry base) |
| $SiO_2/Al_2O_3$ (molar ratio) | 6.2 | (dry base) |
| $K_2O$ | 15.9% by weight | (dry base) |

EXAMPLE 2

The reaction was conducted in the same manner as in Example 1 except that chlorobenzene was used instead of benzene and chlorine was supplied for 4 hours. As the resuls, the conversion of chlorobenzene was 97.5%, the yield of p-dichlorobenzene was 85.6%, the production ratio of o-dichlorobenzene/p-dichlorobenzene (i.e. o/p ratio) was 0.124, and trichlorobenzene was 0.6%.

EXAMPLES 3 AND 4

The reactions were conducted in the same manner as in Example 2 except the bromobenzene and fluorobenzene were used, respectively. The results thereby obtained are shown in the following Table 1. In the Table, the o/p ratio represents a production ratio of o-chlorohalobenzene/p-chlorohalobenzene.

TABLE 1

| Examples | Benzenes | Conversion(%) | Yield of p-chlorohalobenzene | o/p ratio |
|---|---|---|---|---|
| 3 | Bromobenzene | 95 | p-Chlorobromobenzene 80.9% | 0.12 |
| 4 | Fluorobenzene | 99.7 | p-Chlorofluorobenzene 97.0% | 0.026 |

COMPARATIVE EXAMPLE 1

The reaction was conducted in the same manner as in Example 1 except that the L-type zeolite was replaced by Y-type zeolite (tradename: TSZ-301, manufactured by Toyo Soda Manufacturing Co., Ltd.). As the results, the conversion of benzene was 100 %, the yield of g-dichlorobenzene was 71.8 %, the production ratio of o-dichlorobenzene/p-dichlorobenzene (i.e. o/p ratio) was 0.354, and trichlorobenzene was 1.3 %.

The Y-type zeolite used for the reaction, had the following chemical composition (as measured by an atomic absorptiometric method).

| | | |
|---|---|---|
| $SiO_2$ | 66.5% by weight | (dry base) |
| $Al_2O_3$ | 21.6% by weight | (dry base) |
| $Na_2O$ | 12.5% by weight | (dry base) |
| $SiO_2/Al_2O_3$ (molar ratio) | 5.2 | (dry base) |

We claim:

1. A process for producing a chlorohalobenzene of the formula:

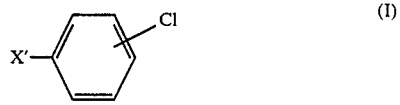

with high selectivity for p-chlorohalobenzene, wherein X' is halogen; comprising: chlorinating a benzene of the formula: chlorinating a benzene of the formula:

wherein:
X is hydrogen or halogen, at a temperature of from 0° C. to a temperature not higher than the boiling point of the benzene in the liquid phase in the presence of a L-type zeolite catalyst,
wherein the chlorinating agent used in chlorine gas, sulfuryl chloride, N-chlorosuccimide, phosphorus pentachloride or chlorine monoxide.

2. The process according to claim 1, wherein the benzene of formula II is selected from the group consisting of benzene, chlorobenzene, bromobenzene, fluorobenzene and iodobenzene.

3. The process according to claim 1, wherein the L-type zeolite is a crystalline alumina silicate having a molar ratio of $SiO_2/Al_2O_3$ being from 4 to 8.

4. The process according to claim 1, wherein the L-type zeolite is used in an amount of at least 0.1 g per mol of the benzene.

5. The process according to claim 1, wherein the L-type zeolite is used in an amount of from 0.1 to 50 g per mol of the benzene.

6. The process according to claim 1, wherein the chlorination is conducted at a temperature within a range of from 20° C. to the boiling point of the benzene.

7. The process according to the claim 1, wherein the chlorination is conducted at a temperature of from 20 to 90° C.

8. The process according to claim 1, wherein the chlorohalobenzene of the general formula I is a p-dichlorobenzene.

9. The process according to claim 1, wherein benzene is chlorinated to obtain p-dichlorobenzene.

10. The process according to claim 1, wherein chlorobenzene is chlorinated to obtain p-dichlorobenzene.

11. A process for producing a p-chlorohalobenzene from benzene or a halobenzene, said process comprising:
(i) chlorinating benzene or a halobenzene, in the presence of a L-type zeolite catalyst at a temperature within the range of from 0° C. to the boiling point of said benzene or said halobenzene and using as a chlorinating agent chlorine gas, sulfurochloride, N-chlorosuccimide, phosphorus pentachloride or chlorine monoxide and; and
(ii) obtaining a p-chlorohalobenzene.

12. The process of claim 11, comprising:
(i) using as said benzene or said halobenzene at least one member selected from the group consisting of benzene, chlorobenzene, bromobenzene, fluorobenzene, and iodobenzene, wherein said temperature is within the range of from 20 to 90° C., and
(ii) obtaining a p-chlorohalobenzene.

13. The process of claim 11, wherein benzene, chlorobenzene, bromobenzene, fluorobenzene, or iodobenzene is used, and the said chlorinating agent is chlorine gas.

14. A process for producing a p-chlorohalobenzene from benzene or a halobenzene, said process comprising:
(i) chlorinating at least one member selected from the group consisting of benzene, chlorobenzene, bromobenzene, fluorobenzene, and iodobenzene, using a temperature of at least 0° C. and no higher than the boiling point of said benzene or halobenzene, using a zeolite catalyst, and a chlorinating agent which is at least one member selected from the group consisting of chlorine gas, sulfurochloride, N-chlorosuccimide, phosphorus pentachloride, and chlorine monoxide, and wherein the said zeolite is a L-zeolite which is a crystalline alumina silicate having a $SiO_2/Al_2O_3$ molar ratio of from 4 to 8 or a synthetic or natural zeolite having a X-ray diffraction spectrum which is the same as the X-ray diffraction spectrum of the said L-zeolite; and
(ii) obtaining a p-chlorohalobenzene.

15. The process of claim 11, comprising:
(i) chlorinating benzene, or chlorobenzene, wherein the chlorinating agent is chlorine; and
(ii) obtaining a p-chlorohalobenzene.

* * * * *